(12) United States Patent
Deur-Bert et al.

(10) Patent No.: US 11,008,268 B2
(45) Date of Patent: May 18, 2021

(54) METHOD FOR PRODUCING FLUORINATED COMPOUNDS

(71) Applicant: Arkema France, Colombes (FR)

(72) Inventors: Dominique Deur-Bert, Charly (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/757,649

(22) PCT Filed: Nov. 5, 2018

(86) PCT No.: PCT/FR2018/052714
§ 371 (c)(1),
(2) Date: Apr. 20, 2020

(87) PCT Pub. No.: WO2019/086816
PCT Pub. Date: May 9, 2019

(65) Prior Publication Data
US 2020/0325088 A1    Oct. 15, 2020

(30) Foreign Application Priority Data
Nov. 6, 2017 (FR) ..................... 1760376

(51) Int. Cl.
*C07C 17/20* (2006.01)
*C07C 21/18* (2006.01)

(52) U.S. Cl.
CPC ............ *C07C 17/206* (2013.01); *C07C 21/18* (2013.01)

(58) Field of Classification Search
CPC ........ C07C 17/25; C07C 21/18; C07C 17/206
See application file for complete search history.

(56) References Cited

U.S. PATENT DOCUMENTS

| | | |
|---|---|---|
| 6,034,288 A | 3/2000 | Scott et al. |
| 2014/0215970 A1 | 8/2014 | Bektesevic et al. |
| 2014/0275647 A1 | 9/2014 | Merkel et al. |
| 2015/0203422 A1 | 7/2015 | Deur-Bert et al. |
| 2016/0251282 A1 | 9/2016 | Bonnet et al. |

FOREIGN PATENT DOCUMENTS

| | | |
|---|---|---|
| WO | 94/23813 A1 | 10/1994 |
| WO | 2013/088195 A1 | 6/2013 |
| WO | 2014/120865 A1 | 8/2014 |
| WO | 2015/055927 A1 | 4/2015 |

OTHER PUBLICATIONS

ISA/EP; International Search Report and Written Opinion for International Patent Application No. PCT/FR2018/052714 dated Apr. 2, 2019, 13 pages.

*Primary Examiner* — Jafar F Parsa
(74) *Attorney, Agent, or Firm* — NK Patent Law (57) ABSTRACT

The present invention relates to a process for producing a fluorinated compound, comprising the steps of providing a gas stream comprising hydrofluoric acid; providing at least one liquid stream of chlorinated compound; spraying said at least one liquid stream of chlorinated compound to form droplets; vaporizing said droplets produced in step c) by mixing with said gas stream, the resulting mixture being a gas mixture; catalytic reaction of the chlorinated compound with the hydrofluoric acid in the gas phase and collection of a product stream; characterized in that the droplets produced in step c) have a mean diameter of less than 500 μm. The invention also relates to a facility for performing this process.

10 Claims, 3 Drawing Sheets

METHOD FOR PRODUCING FLUORINATED COMPOUNDS

CROSS-REFERENCE TO RELATED APPLICATIONS

This application is a U.S. National Stage application of International Patent Application No. PCT/FR2018/052714, filed on Nov. 5, 2018, which claims the benefit of French Patent Application No. 1760376, filed on Nov. 6, 2017.

TECHNICAL FIELD OF THE INVENTION

The present invention relates to a process for producing fluorinated compounds, for instance hydrofluoroolefins or hydrofluorocarbons, and to a facility that is suitable for performing this process.

TECHNICAL BACKGROUND OF THE INVENTION

It is known practice to produce hydrofluoroolefins or hydrofluorocarbons notably by fluorination of hydrochloroolefins or of hydrochlorocarbons. This fluorination is generally a catalytic fluorination using hydrofluoric acid as fluorinating agent.

The fluorination reaction must generally be performed at a high temperature (more than 300° C.) in the gas phase. Consequently, it is known practice to heat, vaporize and superheat the reagents before the fluorination reaction, using heat exchangers.

However, this preliminary step of heating, vaporizing and superheating the reagents has a tendency to lead to the production of coke in the heat exchangers. WO 2014/120865 discloses a process for reducing the decomposition of chlorinated compounds. WO 2015/055927 discloses a process for producing fluorinated compounds from chlorinated compounds, the latter being vaporized. U.S. Pat. No. 6,034,288 also discloses a process for vaporizing halocarbides.

There is thus a need to develop a process for producing fluorinated compounds which limits or avoids the problem of coking of the facility.

SUMMARY OF THE INVENTION

According to a first aspect, the invention relates to a process for producing a fluorinated compound, comprising the steps of:
a) providing a gas stream comprising hydrofluoric acid;
b) providing at least one liquid stream of chlorinated compound;
c) spraying said at least one liquid stream of chlorinated compound to form droplets;
d) vaporizing said droplets produced in step c) by mixing with said gas stream, the resulting mixture being a gas mixture;
e) catalytic reaction of the chlorinated compound with the hydrofluoric acid in the gas phase and collection of a product stream;
characterized in that the droplets produced in step c) have a mean diameter of less than 500 µm.

According to a preferred embodiment, the droplets produced have a mean diameter of less than 150 µm, preferably less than 100 µm.

According to a preferred embodiment, more than 90% of the droplets produced have a mean diameter of less than 500 µm.

According to a preferred embodiment, the chlorinated compound is a chlorocarbon, a hydrochlorocarbon, a chlorofluorocarbon, a hydrochlorofluorocarbon, a chloroolefin, a hydrochloroolefin, a chlorofluoroolefin or a hydrochlorofluoroolefin; and in which the fluorinated compound is a fluorocarbon, a hydrofluorocarbon, a chlorofluorocarbon, a hydrochlorofluorocarbon, a fluoroolefin, a hydrofluoroolefin, a chlorofluoroolefinic or a hydrochlorofluoroolefin; preferably, the chlorinated compound is chosen from 1,1,2-trichloroethane, 1,1,1,2,3-pentachloropropane, 1,1,1,3,3-pentachloropropane, 1,1,2,2,3-pentachloropropane, 2,3-dichloro-1,1,1-trifluoropropane, perchloroethylene, 1,2-dichloroethylene, 1,1,2,3-tetrachloropropene, 2,3,3,3-tetrachloropropene, 1,1,3,3-tetrachloropropene, 1,3,3,3-tetrachloropropene, 2-chloro-3,3,3-trifluoropropene, 1-chloro-3,3,3-trifluoropropene and mixtures thereof; more preferentially, the fluorinated compound is chosen from pentafluoroethane, 1-chloro,2,2-difluoroethane, 1,3,3,3-tetrafluoropropene, 2,3,3,3-tetrafluoropropene, 2-chloro-3,3,3-trifluoropropene, 1-chloro-3,3,3-trifluoropropene, 1,1,1,2,2-pentafluoropropane, 1,1,1,3,3-pentafluoropropane and mixtures thereof; more particularly preferably, the chlorinated compound is perchloroethylene and the fluorinated compound is pentafluoroethane, or the chlorinated compound is 1,1,1,2,3-pentachloropropane and the fluorinated compound is 2,3,3,3-tetrafluoropropene.

According to a preferred embodiment, steps c) and d) are used in a spraying, vaporizing and mixing unit, said unit being a static mixer comprising one or more spraying nozzles equipped with orifices suitable for allowing the formation of droplets with a mean diameter of less than 500 µm.

According to one embodiment, the process also comprises one or more steps of separating the product stream, allowing the collection, firstly, of a stream of the fluorinated compound and, secondly, a recycling stream; preferably, the recycling stream provides the gas stream comprising hydrofluoric acid, optionally after an input of hydrofluoric acid or, preferably, a step of catalytic fluorination of the recycling stream is performed, where appropriate with an input of hydrofluoric acid, the gas stream comprising hydrofluoric acid being collected on conclusion of this fluorination step.

According to a preferred embodiment, the process also comprises a step of heating the liquid stream of chlorinated compound to a temperature below the vaporization temperature of said compound.

According to a preferred embodiment, the process comprises, after step d), and before step e):
a step of heating the mixture; or
a step of cooling the mixture.

According to a second aspect, the invention relates to a facility for producing a fluorinated compound, comprising:
a pipe for supplying the liquid stream of chlorinated compound;
a pipe for supplying the gas stream comprising hydrofluoric acid;
a spraying, vaporizing and mixing unit fed by the pipe for supplying the liquid stream of chlorinated compound and the pipe for supplying the gas stream comprising hydrofluoric acid;
a pipe for collecting the gas mixture at the outlet of the spraying, vaporizing and mixing unit;
a catalytic fluorination reactor fed by the gas mixture collection pipe; and
a pipe for collecting the product stream at the outlet of the catalytic fluorination reactor;

characterized in that the spraying, vaporizing and mixing unit is a static mixer comprising one or more spraying nozzles equipped with orifices suitable for allowing the formation of droplets with a mean diameter of less than 500 µm.

According to a preferred embodiment, the fluorinated compound is a chlorocarbon, a hydrochlorocarbon, a chlorofluorocarbon, a hydrochlorofluorocarbon, a chloroolefin, a hydrochloroolefin or a hydrochlorofluoroolefin; and in which the fluorinated compound is a fluorocarbon, a hydrofluorocarbon, a chlorofluorocarbon, a hydrochlorofluorocarbon, a fluoroolefin, a hydrofluoroolefin or a hydrochlorofluoroolefin; preferably, the chlorinated compound is chosen from 1,1,2-trichloroethane, 1,1,1,2,3-pentachloropropane, 1,1,1,3,3-pentachloropropane, 1,1,2,2,3-pentachloropropane, 2,3-dichloro-1,1,1-trifluoropropane, perchloroethylene, 1,2-dichloroethylene, 1,1,2,3-tetrachloropropene, 2,3,3,3-tetrachloropropene, 1,1,3,3-tetrachloropropene, 1,3,3,3-tetrachloropropene, 2-chloro-3,3,3-trifluoropropene, 1-chloro-3,3,3-trifluoropropene and mixtures thereof; more preferentially, the fluorinated compound is chosen from pentafluoroethane, 1-chloro,2,2-difluoroethane, 1,3,3,3-tetrafluoropropene, 2,3,3,3-tetrafluoropropene, 2-chloro-3,3,3-trifluoropropene, 1-chloro-3,3,3-trifluoropropene, 1,1,1,2,2-pentafluoropropane, 1,1,1,3,3-pentafluoropropane and mixtures thereof; more particularly preferably, the chlorinated compound is perchloroethylene and the fluorinated compound is pentafluoroethane, or the chlorinated compound is 1,1,1,2,3-pentachloropropane and the fluorinated compound is 2,3,3,3-tetrafluoropropene.

According to a preferred embodiment, the facility comprises at least one separation unit fed by the product stream collection pipe; and a fluorinated compound collection pipe and a recycling stream collection pipe at the outlet of the separation unit(s).

According to a preferred embodiment, the recycling stream collection pipe and optionally a hydrofluoric acid supply pipe feed the pipe for supplying the gas stream comprising hydrofluoric acid.

According to a preferred embodiment, the facility comprises a catalytic fluorination reactor at least partly fed by the recycling stream collection pipe, where appropriate with an input of hydrofluoric acid, the pipe for supplying the gas stream comprising hydrofluoric acid being derived from the catalytic fluorination reactor.

According to a preferred embodiment, the facility comprises heating means on the pipe for supplying the liquid stream of chlorinated compound. Said heating means allow the liquid stream of chlorinated compound to be heated, without vaporizing it, said stream remaining in liquid form.

According to a preferred embodiment, the facility comprises heating means or cooling means on the gas mixture collection pipe.

The present invention makes it possible to overcome the drawbacks of the prior art. It more particularly provides a process for producing fluorinated compounds which limits or avoids the problem of coking of the facility.

This is accomplished by specifically spraying the main reagent (chlorinated compound intended to be fluorinated) to form droplets with a specific mean diameter, followed by vaporizing the droplets formed while mixing them with a hot gas stream which contains hydrofluoric acid. The problems associated with incomplete or late vaporization of the chlorinated compound, these two factors promoting coking, are overcome by specifically limiting the size of the droplets.

DETAILED DESCRIPTION OF THE INVENTION

The invention is now described in greater detail and in a nonlimiting manner in the description that follows.

According to a first aspect of the present invention, a process for producing a fluorinated compound is provided. Said process comprises the steps of:
 a) providing a gas stream comprising hydrofluoric acid;
 b) providing at least one liquid stream of chlorinated compound;
 c) spraying said at least one liquid stream of chlorinated compound to form droplets;
 d) vaporizing said droplets produced in step c) by mixing with said gas stream, the resulting mixture being a gas mixture;
 e) catalytic reaction of the chlorinated compound with the hydrofluoric acid in the gas phase and collection of a product stream.

Preferably, the droplets produced in step c) have a mean diameter of less than 500 µm. Advantageously, the droplets produced in step c) have a mean diameter of less than 450 µm, preferably less than 400 µm, more preferentially less than 350 µm, in particular less than 300 µm, more particularly less than 250 µm, favorably less than 200 µm, advantageously favorably less than 150 µm, preferentially favorably less than 100 µm, particularly favorably less than 75 µm.

According to a preferred embodiment, more than 50% of the droplets produced have a mean diameter of less than 500 µm. Advantageously, more than 55% of the droplets produced in step c) have a mean diameter of less than 500 µm, preferably more than 60% of the droplets produced in step c) have a mean diameter of less than 500 µm, more preferentially more than 65% of the droplets produced in step c) have a mean diameter of less than 500 µm, in particular more than 70% of the droplets produced in step c) have a mean diameter of less than 500 µm, more particularly more than 75% of the droplets produced in step c) have a mean diameter of less than 500 µm, favorably more than 80% of the droplets produced in step c) have a mean diameter of less than 500 µm, advantageously favorably more than 85% of the droplets produced in step c) have a mean diameter of less than 500 µm, preferentially favorably more than 90% of the droplets produced in step c) have a mean diameter of less than 500 µm, particularly favorably more than 95% of the droplets produced in step c) have a mean diameter of less than 500 µm.

According to a preferred embodiment, more than 50% of the droplets produced have a mean diameter of less than 450 µm. Advantageously, more than 55% of the droplets produced in step c) have a mean diameter of less than 450 µm, preferably more than 60% of the droplets produced in step c) have a mean diameter of less than 450 µm, more preferentially more than 65% of the droplets produced in step c) have a mean diameter of less than 450 µm, in particular more than 70% of the droplets produced in step c) have a mean diameter of less than 450 µm, more particularly more than 75% of the droplets produced in step c) have a mean diameter of less than 450 µm, favorably more than 80% of the droplets produced in step c) have a mean diameter of less than 450 µm, advantageously favorably more than 85% of the droplets produced in step c) have a mean diameter of less than 450 µm, preferentially favorably more than 90% of the droplets produced in step c) have a mean diameter of less than 450 µm, particularly favorably more than 95% of the droplets produced in step c) have a mean diameter of less than 450 µm.

According to a preferred embodiment, more than 50% of the droplets produced have a mean diameter of less than 400 µm. Advantageously, more than 55% of the droplets produced in step c) have a mean diameter of less than 400 µm, preferably more than 60% of the droplets produced in step c) have a mean diameter of less than 400 µm, more preferentially more than 65% of the droplets produced in step c) have a mean diameter of less than 400 µm, in particular more than 70% of the droplets produced in step c) have a mean diameter of less than 400 µm, more particularly more than 75% of the droplets produced in step c) have a mean diameter of less than 400 µm, favorably more than 80% of the droplets produced in step c) have a mean diameter of less than 400 µm, advantageously favorably more than 85% of the droplets produced in step c) have a mean diameter of less than 400 µm, preferentially favorably more than 90% of the droplets produced in step c) have a mean diameter of less than 400 µm, particularly favorably more than 95% of the droplets produced in step c) have a mean diameter of less than 400 µm.

According to a preferred embodiment, more than 50% of the droplets produced have a mean diameter of less than 350 µm. Advantageously, more than 55% of the droplets produced in step c) have a mean diameter of less than 350 µm, preferably more than 60% of the droplets produced in step c) have a mean diameter of less than 350 µm, more preferentially more than 65% of the droplets produced in step c) have a mean diameter of less than 350 µm, in particular more than 70% of the droplets produced in step c) have a mean diameter of less than 350 µm, more particularly more than 75% of the droplets produced in step c) have a mean diameter of less than 350 µm, favorably more than 80% of the droplets produced in step c) have a mean diameter of less than 350 µm, advantageously favorably more than 85% of the droplets produced in step c) have a mean diameter of less than 350 µm, preferentially favorably more than 90% of the droplets produced in step c) have a mean diameter of less than 350 µm, particularly favorably more than 95% of the droplets produced in step c) have a mean diameter of less than 350 µm.

According to a preferred embodiment, more than 50% of the droplets produced have a mean diameter of less than 300 µm. Advantageously, more than 55% of the droplets produced in step c) have a mean diameter of less than 300 µm, preferably more than 60% of the droplets produced in step c) have a mean diameter of less than 300 µm, more preferentially more than 65% of the droplets produced in step c) have a mean diameter of less than 300 µm, in particular more than 70% of the droplets produced in step c) have a mean diameter of less than 300 µm, more particularly more than 75% of the droplets produced in step c) have a mean diameter of less than 300 µm, favorably more than 80% of the droplets produced in step c) have a mean diameter of less than 300 µm, advantageously favorably more than 85% of the droplets produced in step c) have a mean diameter of less than 300 µm, preferentially favorably more than 90% of the droplets produced in step c) have a mean diameter of less than 300 µm, particularly favorably more than 95% of the droplets produced in step c) have a mean diameter of less than 300 µm.

According to a preferred embodiment, more than 50% of the droplets produced have a mean diameter of less than 250 µm. Advantageously, more than 55% of the droplets produced in step c) have a mean diameter of less than 250 µm, preferably more than 60% of the droplets produced in step c) have a mean diameter of less than 250 µm, more preferentially more than 65% of the droplets produced in step c) have a mean diameter of less than 250 µm, in particular more than 70% of the droplets produced in step c) have a mean diameter of less than 250 µm, more particularly more than 75% of the droplets produced in step c) have a mean diameter of less than 250 µm, favorably more than 80% of the droplets produced in step c) have a mean diameter of less than 250 µm, advantageously favorably more than 85% of the droplets produced in step c) have a mean diameter of less than 250 µm, preferentially favorably more than 90% of the droplets produced in step c) have a mean diameter of less than 250 µm, particularly favorably more than 95% of the droplets produced in step c) have a mean diameter of less than 250 µm.

According to a preferred embodiment, more than 50% of the droplets produced have a mean diameter of less than 200 µm. Advantageously, more than 55% of the droplets produced in step c) have a mean diameter of less than 200 µm, preferably more than 60% of the droplets produced in step c) have a mean diameter of less than 200 µm, more preferentially more than 65% of the droplets produced in step c) have a mean diameter of less than 200 µm, in particular more than 70% of the droplets produced in step c) have a mean diameter of less than 200 µm, more particularly more than 75% of the droplets produced in step c) have a mean diameter of less than 200 µm, favorably more than 80% of the droplets produced in step c) have a mean diameter of less than 200 µm, advantageously favorably more than 85% of the droplets produced in step c) have a mean diameter of less than 200 µm, preferentially favorably more than 90% of the droplets produced in step c) have a mean diameter of less than 200 µm, particularly favorably more than 95% of the droplets produced in step c) have a mean diameter of less than 200 µm.

According to a preferred embodiment, more than 50% of the droplets produced have a mean diameter of less than 150 µm. Advantageously, more than 55% of the droplets produced in step c) have a mean diameter of less than 150 µm, preferably more than 60% of the droplets produced in step c) have a mean diameter of less than 150 µm, more preferentially more than 65% of the droplets produced in step c) have a mean diameter of less than 150 µm, in particular more than 70% of the droplets produced in step c) have a mean diameter of less than 150 µm, more particularly more than 75% of the droplets produced in step c) have a mean diameter of less than 150 µm, favorably more than 80% of the droplets produced in step c) have a mean diameter of less than 150 µm, advantageously favorably more than 85% of the droplets produced in step c) have a mean diameter of less than 150 µm, preferentially favorably more than 90% of the droplets produced in step c) have a mean diameter of less than 150 µm, particularly favorably more than 95% of the droplets produced in step c) have a mean diameter of less than 150 µm.

According to a preferred embodiment, more than 50% of the droplets produced have a mean diameter of less than 100 µm. Advantageously, more than 55% of the droplets produced in step c) have a mean diameter of less than 100 µm, preferably more than 60% of the droplets produced in step c) have a mean diameter of less than 100 µm, more preferentially more than 65% of the droplets produced in step c)

have a mean diameter of less than 100 µm, in particular more than 70% of the droplets produced in step c) have a mean diameter of less than 100 µm, more particularly more than 75% of the droplets produced in step c) have a mean diameter of less than 100 µm, favorably more than 80% of the droplets produced in step c) have a mean diameter of less than 100 µm, advantageously favorably more than 85% of the droplets produced in step c) have a mean diameter of less than 100 µm, preferentially favorably more than 90% of the droplets produced in step c) have a mean diameter of less than 100 µm, particularly favorably more than 95% of the droplets produced in step c) have a mean diameter of less than 100 µm.

According to a preferred embodiment, more than 50% of the droplets produced have a mean diameter of less than 75 µm. Advantageously, more than 55% of the droplets produced in step c) have a mean diameter of less than 75 µm, preferably more than 60% of the droplets produced in step c) have a mean diameter of less than 75 µm, more preferentially more than 65% of the droplets produced in step c) have a mean diameter of less than 75 µm, in particular more than 70% of the droplets produced in step c) have a mean diameter of less than 75 µm, more particularly more than 75% of the droplets produced in step c) have a mean diameter of less than 75 µm, favorably more than 80% of the droplets produced in step c) have a mean diameter of less than 75 µm, advantageously favorably more than 85% of the droplets produced in step c) have a mean diameter of less than 75 µm, preferentially favorably more than 90% of the droplets produced in step c) have a mean diameter of less than 75 µm, particularly favorably more than 95% of the droplets produced in step c) have a mean diameter of less than 75 µm.

Figure 1:
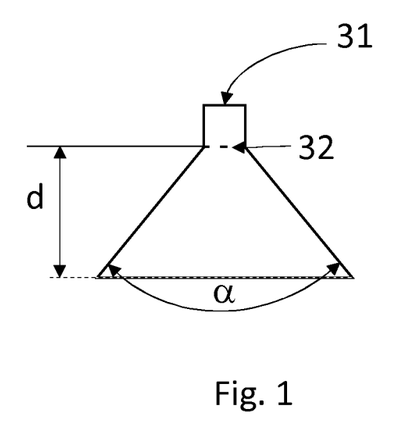
FIG. 1 represents the spraying angle α of a nozzle which serves to spray the liquid stream as droplets.

Preferably, said droplets produced in step c) are sprayed at a spraying angle α of from 10° to 180°, preferably from 20° to 170°, in particular from 30° to 165°. The spraying angle α corresponds to the angle of the jet emitted by an orifice 32 of a nozzle 31 determined at a distance of 10 cm from the set of orifices 32 of said nozzle 31 under consideration (FIG. 1).

Preferably, the ratio R between the volume-median diameter (VMD) and the number-median diameter (NMD) is between 1 and 3, preferably between 1 and 2.5, in particular between 1.2 and 2. The volume-median diameter is the droplet diameter which divides all of the other droplets into two groups of equal volume, one consisting of larger droplets and the other of smaller droplets. The number-median diameter is the droplet diameter on either side of which is found 50% of the total number of droplets. The closer to 1 the value of R, the more the droplet sizes are similar.

Preferably, the nozzle is made of a material that is resistant to hydrofluoric acid, for instance 316L stainless steel, alloys of the type such as Monel®, Inconel® or Hastelloy® or nickel-based alloys.

Moreover, as a result of this mixing step, the partial pressure of the chlorinated compound during its vaporization is relatively moderate, and thus the vaporization temperature is also relatively moderate, and in any case below the vaporization temperature in the situation in which the chlorinated compound is independently vaporized. This notably makes it possible to limit the risks of degradation of the chlorinated compound that can give rise to coke formation.

Preferably, the gas stream comprising hydrofluoric acid is at a temperature of from 100 to 400° C., more particularly from 130 to 380° C. and advantageously from 250 to 380° C. at the moment of its mixing with the liquid stream of chlorinated compound.

In general, the temperature of the gas stream comprising hydrofluoric acid, at the moment of its mixing with the liquid stream of chlorinated compound, is chosen to be:
  less than, greater than or equal to the temperature of the catalytic reaction;
  greater than or equal to the vaporization temperature of the gas stream comprising hydrofluoric acid, which depends on the pressure and composition of this stream (notably the HF content).

For example, in the context of producing HFO-1234yf (as described in detail below), the temperature of the gas stream comprising hydrofluoric acid may be from about 320 to 380° C.

As mentioned above, the invention relates to the fluorination of a chlorinated compound with hydrofluoric acid, to form a fluorinated compound.

The term "chlorinated compound" means an organic compound comprising one or more chlorine atoms, and the term "fluorinated compound" means an organic compound comprising one or more fluorine atoms.

It is understood that the chlorinated compound may comprise one or more fluorine atoms, and that the fluorinated compound may comprise one or more chlorine atoms. In general, the number of chlorine atoms in the fluorinated compound is less than the number of chlorine atoms in the chlorinated compound; and the number of fluorine atoms in the fluorinated compound is greater than the number of fluorine atoms in the chlorinated compound.

The chlorinated compound may be an alkane or an alkene optionally bearing substituents chosen from F, Cl, I and Br (preferably from F and Cl), and comprising at least one Cl substituent.

The fluorinated compound may be an alkane or an alkene optionally bearing substituents chosen from F, Cl, I and Br (preferably from F and Cl), and comprising at least one F substituent.

The chlorinated compound may notably be an alkane with one or more chlorine substituents (hydrochlorocarbon or chlorocarbon) or an alkane with one or more chlorine and fluorine substituents (hydrochlorofluorocarbon or chlorofluorocarbon) or an alkene with one or more chlorine substituents (chloroolefin or hydrochloroolefin) or an alkene with one or more chlorine and fluorine substituents (hydrochlorofluoroolefin or chlorofluoroolefin).

The fluorinated compound may notably be an alkane with one or more fluorine substituents (fluorocarbon or hydrofluorocarbon) or an alkane with one or more chlorine and fluorine substituents (hydrochlorofluorocarbon or chlorofluorocarbon) or an alkene with one or more fluorine substituents (fluoroolefin or hydrofluoroolefin) or an alkene with one or more chlorine and fluorine substituents (hydrochlorofluoroolefin or chlorofluoroolefin).

The chlorinated compound and the fluorinated compound may be linear or branched, preferably linear.

According to one embodiment, the chlorinated compound and the fluorinated compound include only one carbon atom.

According to one embodiment, the chlorinated compound and the fluorinated compound include two carbon atoms.

According to one embodiment, the chlorinated compound and the fluorinated compound include three carbon atoms.

According to one embodiment, the chlorinated compound and the fluorinated compound include four carbon atoms.

According to one embodiment, the chlorinated compound and the fluorinated compound include five carbon atoms.

The invention is notably found to apply to the following fluorination reactions:

fluorination of perchloroethylene (PER) to give pentafluoroethane (HFC-125);
fluorination of 1,1,1,2,3-pentachloropropane (HCC-240db) to give 2-chloro-3,3,3-trifluoropropene (HCFO-1233xf);
fluorination of 1,1,1,2,3-pentachloropropane (HCC-240db) to give 2,3,3,3-tetrafluoropropene (HFO-1234yf);
fluorination of 1,1,1,2,3-pentachloropropane (HCC-240db) to give 1,1,1,2,2-pentafluoropropane (HFC-245cb);
fluorination of 1,1,1,3,3-pentachloropropane (HCC-240fa) to give 1,3,3,3-tetrafluoropropene (HFO-1234ze);
fluorination of 1,1,1,3,3-pentachloropropane (HCC-240fa) to give 1-chloro-3,3,3-trifluoropropene (HCFO-1233zd);
fluorination of 1,1,1,3,3-pentachloropropane (HCC-240fa) to give 1,1,1,3,3-pentafluoropropane (HFC-245fa);
fluorination of 2-chloro-3,3,3-trifluoropropene (HCFO-1233xf) to give 2,3,3,3-tetrafluoropropene (HFO-1234yf);
fluorination of 2-chloro-3,3,3-trifluoropropene (HCFO-1233xf) to give 1,1,1,2,2-pentafluoropropane (HFC-245cb);
fluorination of 1-chloro-3,3,3-trifluoropropene (HCFO-1233zd) to give 1,1,1,3,3-pentafluoropropane (HFC-245fa);
fluorination of 1,3,3,3-tetrachloropropene (HFO-1234ze) to give 1,1,1,3,3-pentafluoropropane (HFC-245fa);
fluorination of 1,2,2,3-pentachloropropane (HCC-240aa) to give 2,3,3,3-tetrafluoropropene (HFO-1234yf);
fluorination of 1,2,2,3-pentachloropropane (HCC-240aa) to give 1,1,1,2,2-pentafluoropropane (HFC-245cb);
fluorination of 1,2,2,3-pentachloropropane (HCC-240aa) to give 2-chloro-3,3,3-trifluoropropene (HCFO-1233xf);
fluorination of 2,3-dichloro-1,1,1-trifluoropropane (HCFC-243db) to give 2,3,3,3-tetrafluoropropene (HFO-1234yf);
fluorination of 2,3-dichloro-1,1,1-trifluoropropane (HCFC-243db) to give 1-chloro-3,3,3-trifluoropropene (HCFO-1233zd);
fluorination of 2,3-dichloro-1,1,1-trifluoropropane (HCFC-243db) to give 1,3,3,3-tetrafluoropropene (HFO-1234ze);
fluorination of 2,3-dichloro-1,1,1-trifluoropropane (HCFC-243db) to give 2-chloro-3,3,3-trifluoropropene (HCFO-1233xf);
fluorination of 2,3-dichloro-1,1,1-trifluoropropane (HCFC-243db) to give 1,1,1,2,2-pentafluoropropane (HFC-245cb);
fluorination of 3,3-dichloro-1,1,1-trifluoropropane (HCFC-243fa) to give 1-chloro-3,3,3-trifluoropropene (HCFO-1233zd);
fluorination of 3,3-dichloro-1,1,1-trifluoropropane (HCFC-243fa) to give 1,3,3,3-tetrafluoropropene (HFO-1234ze);
fluorination of 3,3-dichloro-1,1,1-trifluoropropane (HCFC-243fa) to give 1,1,1,3,3-pentafluoropropane (HFC-245fa);
fluorination of 1,1,2,3-tetrachloropropene (HCO-1230xa) to give 2,3,3,3-tetrafluoropropene (HFO-1234yf);
fluorination of 1,1,2,3-tetrachloropropene (HCO-1230xa) to give 1,1,1,2,2-pentafluoropropane (HFC-245cb);
fluorination of 1,1,2,3-tetrachloropropene (HCO-1230xa) to give 2-chloro-3,3,3-trifluoropropene (HCFO-1233xf);
fluorination of 2,3,3,3-tetrachloropropene (HCO-1230xf) to give 2,3,3,3-tetrafluoropropene (HFO-1234yf);
fluorination of 2,3,3,3-tetrachloropropene (HCO-1230xf) to give 1,1,1,2,2-pentafluoropropane (HFC-245cb);
fluorination of 2,3,3,3-tetrachloropropene (HCO-1230xf) to give 2-chloro-3,3,3-trifluoropropene (HCFO-1233xf);
fluorination of 1,1,3,3-tetrachloropropene (HCO-1230za) to give 1-chloro-3,3,3-trifluoropropene (HCFO-1233zd);
fluorination of 1,1,3,3-tetrachloropropene (HCO-1230za) to give 1,3,3,3-tetrafluoropropene (HFO-1234ze);
fluorination of 1,1,3,3-tetrachloropropene (HCO-1230za) to give 1,1,1,3,3-pentafluoropropane (HFC-245fa);
fluorination of 1,3,3,3-tetrachloropropene (HCO-1230zd) to give 1,1,1,3,3-pentafluoropropane (HFC-245fa);
fluorination of 1,3,3,3-tetrachloropropene (HCO-1230zd) to give 1-chloro-3,3,3-trifluoropropene (HCFO-1233zd);
fluorination of 1,3,3,3-tetrachloropropene (HCO-1230zd) to give 1,3,3,3-tetrafluoropropene (HFO-1234ze);
fluorination of 1-chloro-3,3,3-trifluoropropene (HCFO-1233zd) to give 1,3,3,3-tetrafluoropropene (HFO-1234ze);
fluorination of 1,1,2-trichloroethane to give 1-chloro-2,2-difluoroethane (HCFC-142);
fluorination of 1,2-dichloroethylene to give 1-chloro-2,2-difluoroethane (HCFC-142).

The conversion of the chlorinated compound into the fluorinated compound may be a direct conversion (with just one reaction step or with just one set of reaction conditions) or an indirect conversion (with two or more than two reaction steps or by using two or more than two sets of reaction conditions).

The fluorination reaction may be performed:
with an HF/chlorinated compound mole ratio of from 1:1 to 150:1, preferably from 2:1 to 125:1 and more particularly preferably from 3:1 to 100:1;
with a contact time from 1 to 100 seconds, preferably 2 to 75 seconds and more particularly 3 to 50 seconds (volume of catalyst divided by the total entering stream, adjusted to the operating temperature and pressure);
at an absolute pressure ranging from atmospheric pressure to 20 bara, preferably from 2 to 18 bara and more preferentially from 3 to 15 bara;
at a temperature (temperature of the catalytic bed) from 200 to 450° C., preferably from 250 to 400° C. and more particularly from 280 to 380° C.

The fluorination reaction is performed in the presence of a catalytic composition. The catalytic composition comprises a chromium-based catalyst. Preferably, the chromium-based catalyst may be a chromium oxide (for example $CrO_2$, $CrO_3$ or $Cr_2O_3$), a chromium oxyfluoride or a chromium fluoride (for example $CrF_3$) or a mixture thereof. The chromium oxyfluoride may have a fluorine content of between 1% and 60% by weight on the basis of the total weight of the chromium oxyfluoride, advantageously between 5% and 55% by weight, preferably between 10% and 52% by weight, more preferentially between 15% and 52% by weight, in particular between 20% and 50% by weight, more particularly between 25% and 45% by weight, favorably between 30% and 45% by weight, more favorably from 35% to 45% by weight of fluorine on the basis of the total weight of chromium oxyfluoride. The catalytic composition may also comprise a cocatalyst chosen from the group consisting of Ni, Co, Zn, Mg, Mn, Fe, Zn, Ti, V, Zr, Mo, Ge, Sn, Pb, Sb; preferably Ni, Co, Zn, Mg, Mn; in particular Ni, Co, Zn. The weight content of the cocatalyst is between 1% and 10% by weight on the basis of the total weight of the catalytic composition. The catalytic composition may also comprise a support such as alumina, for example in its alpha form, activated alumina, aluminum halides (for example $AlF_3$), aluminum oxyhalides, active charcoal, magnesium fluoride or graphite. Preferably, the catalytic composition has a specific surface area of between 1 and 100 $m^2$/g, preferably between 5 and 80 $m^2$/g, more preferentially between 5 and 70 $m^2$/g, ideally between 5 and 50 $m^2$/g, in particular between 10 and 50 $m^2$/g, more particularly between 15 and 45 $m^2$/g.

In order to avoid the activation of the catalyst during the reaction, an oxidizing agent (for example oxygen or chlorine) may be added, for example in an oxidizing agent/organic compounds mole ratio of from 0.005 to 2, preferably from 0.01 to 1.5. It is possible, for example, to use a stream of pure oxygen or of pure chlorine, or an oxygen/nitrogen or chlorine/nitrogen mixture.

Before its use, the catalytic composition is preferably subjected to activation with air, oxygen or chlorine and/or with HF.

Before its use, the catalytic composition is preferably subjected to activation with air or oxygen and HF at a temperature of from 100 to 500° C., preferably from 250 to 500° C. and more particularly from 300 to 400° C. The activation time is preferably from 1 to 200 h and more particularly from 1 to 50 h.

This activation may be followed by a final step of fluorination activation in the presence of an oxidizing agent, of HF and of organic compounds.

The HF/organic compounds mole ratio is preferably from 2 to 40 and the oxidizing agent/organic compounds mole ratio is preferably from 0.04 to 25. The temperature of the final activation is preferably from 300 to 400° C. and its duration is preferably from 6 to 100 h.

Figure 2:
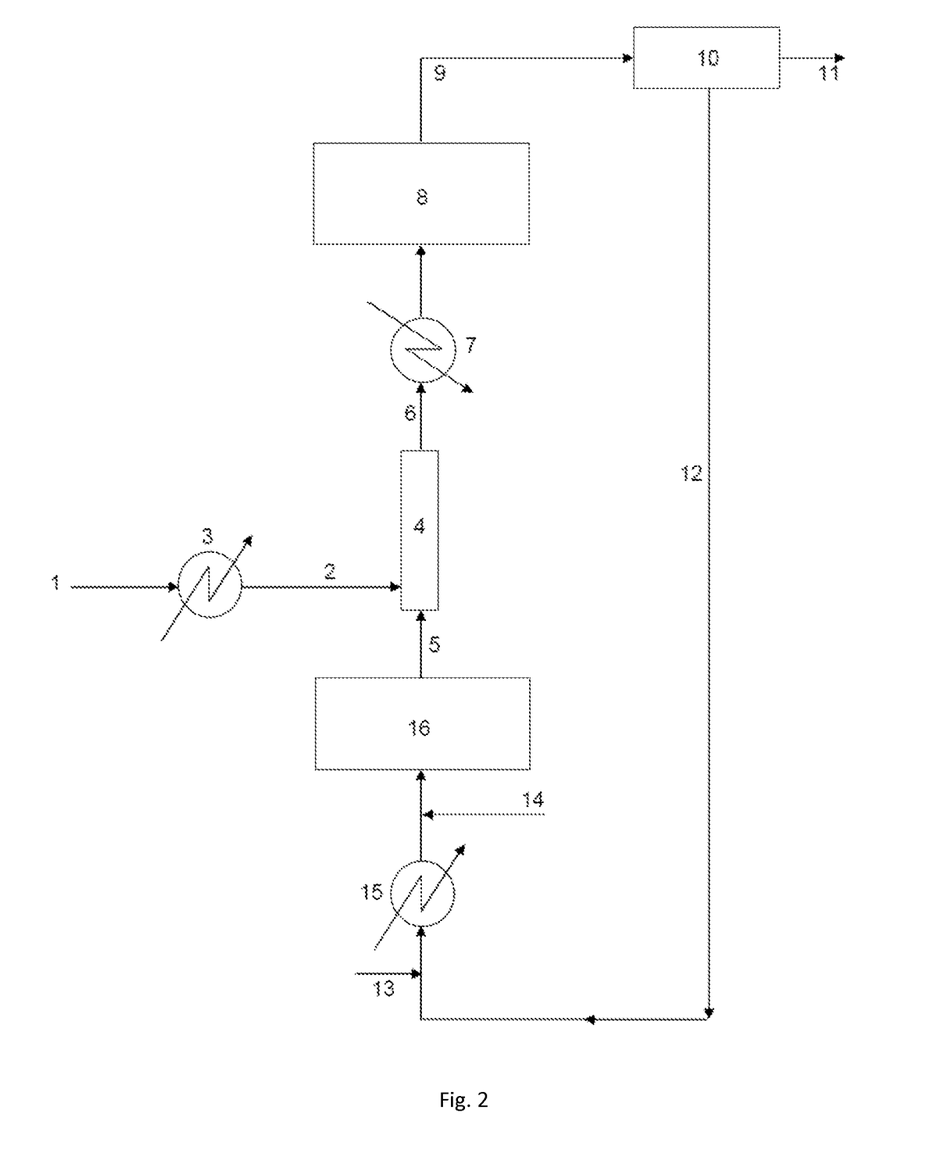
FIG. 2 schematically represents an embodiment of the facility according to the invention.

With reference to FIG. 2, an embodiment of the invention is now described in the particular case of a process for producing HFO-1234yf from HCC-240db, it being understood that it is similarly valid with other chlorinated compounds/fluorinated compounds couples.

The facility according to the invention comprises a pipe for supplying the liquid stream of HCC-240db 2 and a pipe for supplying the gas stream comprising HF 5 which feed a catalytic fluorination reactor 8. The pipe for supplying the liquid stream of HCC-240db 2 is derived from a tank of liquid HCC-240db 1. The pipe for supplying the gas stream comprising HF 5 may transport a stream of pure HF (optionally in combination with an oxidizing agent as described above) or, alternatively, a mixture of HF and of organic compounds, notably of chlorinated and/or fluorinated organic compounds, as is the case in the illustrated example, and as will be described in greater detail hereinbelow.

A spraying, vaporizing and mixing unit 4 is fed both by the pipe for supplying the liquid stream of HCC-240db 2 and the pipe for supplying the gas stream comprising HF 5. This unit is suitable for mixing the gas stream and the liquid stream. It is preferably a static mixer, so as to allow a process of continuous type. The static mixer comprises one or more spraying nozzles equipped with orifices having a specific diameter. Said one or more spraying nozzles allow the spraying of the liquid stream into the static mixer before its vaporization. Preferably, said one or more nozzles have orifices that are suitable for allowing the formation of droplets with a mean diameter of less than 500 µm. Thus, said one or more nozzles may have orifices that are suitable for allowing the formation of droplets with a mean diameter of less than 450 µm, preferably less than 400 µm, more preferentially less than 350 µm, in particular less than 300 µm, more particularly less than 250 µm, favorably less than 200 µm, advantageously favorably less than 150 µm, preferentially favorably less than 100 µm, particularly favorably less than 75 µm. In this unit, the gas stream comprising HF yields heat to the liquid stream of HCC-240db, which allows the vaporization of the HCC-240db. Spraying nozzles having the features mentioned in the present patent application are thus commercially available. The inventors have noted, surprisingly, that the use of nozzles which specifically allow the formation of droplets with a mean diameter of less than 500 µm limits the formation of coke in the equipment such as the heat exchangers, the supply pipes or the catalytic reactor.

The mixture of HCC-240db, of HF and optionally of additional compounds is collected in a gas mixture collection pipe 6 at the outlet of the spraying, vaporizing and mixing unit 4, which transports the mixture to the catalytic fluorination reactor 8.

The HCC-240db may undergo a preliminary heating step before mixing with the gas stream comprising HF. In this case, this preliminary heating is performed at a temperature below the vaporization temperature of the HCC-240db (and at a temperature below the degradation or decomposition temperature of this compound). To this end, heating means 3 may be provided on the pipe for supplying the liquid stream of HCC-240db 2.

Between the mixing of the HCC-240db with the stream comprising HF and the fluorination reaction, it is possible, depending on the case, to provide additional heating of the mixture or, on the contrary, cooling of said mixture, by providing either heating means or, as illustrated in the figure, cooling means 7 on the gas mixture collection pipe 6. The choice of heating or cooling depends on the desired temperature for the fluorination reaction, by comparing with the temperature of the gas mixture obtained from the spraying, vaporizing and mixing unit 4.

A product stream collection pipe 9 is connected at the outlet of the catalytic fluorination reactor 8. Said pipe feeds a separation unit 10 (or several successive separation units) making it notably possible to separate the product of interest (fluorinated compound, in this instance HFO-1234yf) from the rest of the product stream. In this regard, use may notably be made of one or more distillation columns, or of decantation, extraction, washing or other units. This product of interest is recovered in a fluorinated compound collection pipe 11 at the outlet of the separation unit 10. Moreover, a recycling stream is recovered in a recycling stream collection pipe 12. Other undesirable products may moreover be removed at this stage (notably the hydrochloric acid generated during the fluorination reaction).

The recycling stream may notably contain unreacted reagents, namely HF and chlorinated compound (in this instance HCC-240db). It may also contain side products derived from the reaction, i.e. fluorinated compounds obtained by fluorination of the chlorinated compound (HCC-240db) and other than the desired fluorinated compound. In the illustrated case, the recycling stream notably contains HCFO-1233xf, and possibly HFC-245cb (1,1,1,2,2-pentafluoropropane), obtained by fluorination of HCC-240db.

According to one possible embodiment, the recycling stream may be returned directly into the catalytic fluorination reactor 8. According to another possible embodiment, it may undergo an entirely different treatment, or even separate upgrading. According to another possible embodiment, it is partially returned into the catalytic fluorination reactor 8.

According to another embodiment, which is the one illustrated here, the recycling stream undergoes an additional fluorination before being returned to the main catalytic fluorination reactor 8.

Thus, the recycling stream collection pipe 12 feeds an additional catalytic fluorination reactor 16. An HF introduction pipe 13 may, where appropriate, as illustrated, be connected thereto in order to provide fresh HF. An oxidizing agent introduction pipe 14 may also, as illustrated, be connected to the recycling stream collection pipe 12 in order to ensure an input of oxidizing agent for maintaining the catalytic activity of the catalyst.

Heating and vaporizing means 15 may be provided on the recycling stream collection pipe 12 in order to bring the stream to the desired temperature for the additional fluorination reaction, which is performed in the additional catalytic fluorination reactor 16.

In the illustrated example, the pipe for supplying the gas stream comprising HF 5 (described previously) is derived directly from the additional catalytic fluorination reactor 16. Thus, the gas stream comprising HF contains, besides HF (and, where appropriate, the oxidizing agent), fluorinated products obtained from the additional fluorination reaction.

An input of fresh HF and/or an input of oxidizing agent may be added to the pipe for supplying the gas stream comprising HF 5, if need be.

The principle of a production process comprising two different catalytic fluorination steps, feeding with chlorinated reagent (HCC-240db) being performed between these two steps, is described in detail in WO 2013/088195, to which it refers to reference purposes.

The gas stream comprising HF (which is used to vaporize the liquid stream of chlorinated compound) corresponds to a stream derived from an additional fluorination reaction of a recycling stream. Other variants are possible:
- the gas stream comprising HF may be a stream derived from an additional fluorination reaction of a recycling stream, supplemented with additional HF and/or with additional oxidizing agent;
- the gas stream comprising HF may be directly a recycling stream or a partial recycling stream (without an additional fluorination reaction step);
- the gas stream comprising HF may be directly a recycling stream (without an additional fluorination reaction step), supplemented with additional HF and/or with additional oxidizing agent;
- the gas stream comprising HF may be a stream of fresh HF optionally comprising fresh oxidizing agent.

In the latter case, if a recycling stream is present, it may be introduced after the step of mixing the gas stream comprising HF with the liquid stream of chlorinated compound; and, if an additional fluorination reaction of a recycling stream is performed, the stream obtained from this reaction may be introduced after the step of mixing the gas stream comprising HF with the liquid stream of chlorinated compound.

Another embodiment is now described with reference to FIG. 3: this is a process for producing HFC-125 from PER (and also the facility for performing it). The facility includes a pipe for supplying the gas stream comprising HF 25 and a pipe for supplying the liquid stream of PER 21, which both feed a spraying, vaporizing and mixing unit 22, which is a static mixer. The static mixer comprises one or more spraying nozzles equipped with orifices having a specific diameter. Said one or more spraying nozzles allow the spraying of the liquid stream into the static mixer before its vaporization. Preferably, said one or more nozzles have orifices that are suitable for allowing the formation of droplets with a mean diameter of less than 500 μm. Thus, said one or more nozzles may have orifices that are suitable for allowing the formation of droplets with a mean diameter of less than 450 μm, preferably less than 400 μm, more preferentially less than 350 μm, in particular less than 300 μm, more particularly less than 250 μm, favorably less than 200 μm, advantageously favorably less than 150 μm, preferentially favorably less than 100 μm, particularly favorably less than 75 μm. A gas mixture collection pipe 23 is connected to the outlet of the static mixer, said pipe feeding one or a series of several fluorination reactors (not shown). Heating means 26a, 26b, 26c are provided on the pipe for supplying the gas stream comprising HF 25. Heating means 24a, 24b are provided on the gas mixture collection type 23. According to one embodiment, the gas stream comprising HF is obtained by heating and, where appropriate, vaporizing of a recycling stream collected after treatment and separation of a product stream obtained from the catalytic fluorination reaction. Some of the heating means 26a, 24a used may be economizer heat exchangers.

By means of the implementation of the process according to the present invention, the vaporization of the chlorinated compound and its mixing with hydrofluoric acid is performed while substantially limiting the coking. This makes it possible to maintain the productivity of the process at the industrial scale.

EXAMPLES

Example 1 (Comparative)

A facility as described in relation with FIG. 2 is used. A gas stream 5 obtained from a fluorination reactor 8 and comprising HF is mixed with a liquid stream 2 of 240db which has been heated beforehand to a temperature of 120° C. at a pressure of 4 to 6 bara. The flow rate of the gas stream 5 comprising HF obtained from the fluorination reactor is from 20 to 50 kg/hour. This gas stream is at a temperature of from 320° C. to 350° C. and at a pressure of 3 to 5 bara. The flow rate of the liquid stream of 240db is from 3 to 4 kg/hour. Mixing of the two streams is performed in a static mixer 4 not including spraying nozzles (no formation of droplets). After 500 hours, visual inspection of the reactor supply pipe is performed and the formation of coke is observed. In addition, the first layers of the catalytic bed in the reactor also show a deposit of coke.

Example 2 (Invention)

Example 1 is repeated using a static mixer 4 comprising a nozzle whose orifices form droplets with a mean diameter of less than 200 μm. After 500 hours, visual inspection of the reactor supply pipe and of the first layers of the catalytic bed does not reveal any deposit of coke.

Example 3 (Comparative)

Figure 3:
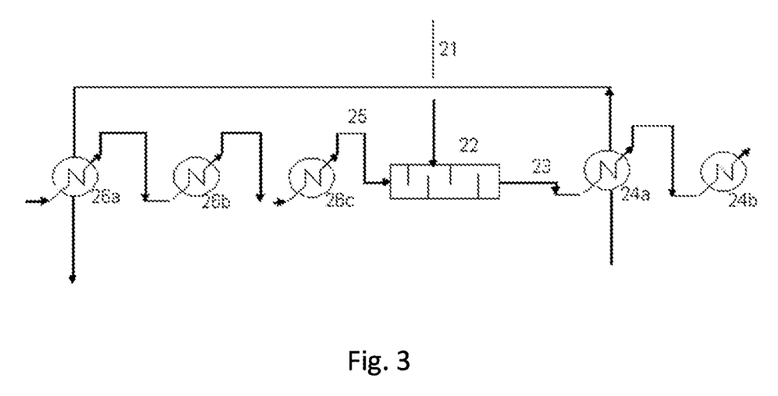
FIG. 3 schematically represents another embodiment of the facility according to the invention.

A facility as described in relation with FIG. 3 is used. The facility includes a pipe for supplying the gas stream comprising HF 25 and a pipe for supplying the liquid stream of perchloroethylene 21, which both feed a static mixer 22. The static mixer 22 comprises a nozzle whose orifices form droplets with a mean diameter of greater than 700 µm. Visual inspection is performed after 1000 hours. The formation of coke on the nozzle and in the static mixer is observed.

Example 4 (Invention)

Example 3 is repeated with a static mixer 22 comprising a nozzle whose orifices form droplets with a mean diameter of less than 200 µm. Visual inspection is performed after 8000 hours. The inspection of the nozzle and of the associated static mixer does not reveal any fouling by coking.

The invention claimed is:

1. A process for producing a fluorinated compound, comprising the steps of:
   a) providing a gas stream comprising hydrofluoric acid;
   b) providing at least one liquid stream of chlorinated compound;
   c) spraying said at least one liquid stream of chlorinated compound to form droplets, wherein the droplets produced in step c) have a mean diameter of less than 500 µm;
   d) vaporizing said droplets produced in step c) by mixing with said gas stream, wherein the resulting mixture is a gas mixture; and
   e) catalytically reacting the chlorinated compound with the hydrofluoric acid in the gas phase and collecting a product stream.

2. The process as claimed in claim 1, wherein the droplets produced have a mean diameter of less than 150 µm.

3. The process as claimed in claim 1, wherein more than 90% of the droplets produced have a mean diameter of less than 500 µm.

4. The process as claimed in claim 1, wherein:
   the chlorinated compound comprises a chlorocarbon, a hydrochlorocarbon, a chlorofluorocarbon, a hydrochlorofluorocarbon, a chloroolefin, a hydrochloroolefin, a chlorofluoroolefin or a hydrochlorofluoroolefin; and
   the fluorinated compound comprises a fluorocarbon, a hydrofluorocarbon, a chlorofluorocarbon, a hydrochlorofluorocarbon, a fluoroolefin, a hydrofluoroolefin, a chlorofluoroolefin or a hydrochlorofluoroolefin.

5. The process as claimed in claim 1, wherein steps c) and d) are used in a spraying, vaporizing and mixing unit, said unit being a static mixer comprising one or more spraying nozzles equipped with orifices configured to allow the formation of droplets with a mean diameter of less than 500 µm.

6. The process as claimed in claim 1, further comprising one or more steps of separating the product stream, allowing the collection, firstly, of a stream of the fluorinated compound and, secondly, a recycling stream.

7. The process as claimed in claim 1, further comprising a step of heating the liquid stream of chlorinated compound to a temperature below the vaporization temperature of said compound.

8. The process as claimed in claim 1, further comprising, after step d), and before step e):
   a step of heating the mixture; or
   a step of cooling the mixture.

9. The process as claimed in claim 4, wherein
   the chlorinated compound comprises 1,1,2-trichloroethane, 1,1,1,2,3-pentachloropropane, 1,1,1,3,3-pentachloropropane, 1,1,2,2,3-pentachloropropane, 2,3-dichloro-1,1,1-trifluoropropane, perchloroethylene, 1,2-dichloroethylene, 1,1,2,3-tetrachloropropene, 2,3,3,3-tetrachloropropene, 1,1,3,3-tetrachloropropene, 1,3,3,3-tetrachloropropene, 2-chloro-3,3,3-trifluoropropene, 1-chloro-3,3,3-trifluoropropene or mixtures thereof; and
   the fluorinated compound comprises pentafluoroethane, 1-chloro,2,2-difluoroethane, 1,3,3,3-tetrafluoropropene, 2,3,3,3-tetrafluoropropene, 2-chloro-3,3,3-trifluoropropene, 1-chloro-3,3,3-trifluoropropene, 1,1,1,2,2-pentafluoropropane, 1,1,1,3,3-pentafluoropropane or mixtures thereof.

10. The process as claimed in claim 6, wherein the recycling stream provides the gas stream comprising hydrofluoric acid, optionally after an input of hydrofluoric acid or a step of catalytic fluorination of the recycling stream is performed, where appropriate with an input of hydrofluoric acid, the gas stream comprising hydrofluoric acid being collected on conclusion of this fluorination step.

* * * * *